United States Patent [19]
Gordon et al.

[11] 3,967,728
[45] July 6, 1976

[54] CATHETER PACKAGE

[75] Inventors: Robert L. Gordon, Monroe, N.Y.;
Burton Salkin, Schaumburg, Ill.

[73] Assignee: International Paper Company, New York, N.Y.

[22] Filed: Feb. 18, 1975

[21] Appl. No.: 550,755

Related U.S. Application Data

[63] Continuation of Ser. No. 337,445, March 2, 1973, abandoned.

[52] U.S. Cl. ............................. 206/364; 206/210; 206/438; 206/484; 206/819; 128/349 R
[51] Int. Cl.² ......................................... A61B 19/02
[58] Field of Search .......... 206/364, 363, 365, 819, 206/210, 212, 438, 484; 128/349 R

[56] References Cited

UNITED STATES PATENTS

| | | | |
|---|---|---|---|
| 2,947,415 | 8/1960 | Garth | 206/364 |
| 3,332,549 | 7/1967 | Powell | 206/363 |
| 3,345,988 | 10/1967 | Vitello | 206/364 |
| 3,556,294 | 1/1971 | Walck | 206/364 |

*Primary Examiner*—George E. Lowrance
*Assistant Examiner*—Joseph M. Moy
*Attorney, Agent, or Firm*—John A. Caruso

[57] ABSTRACT

Disclosed is an improved catheter package wherein the improvement comprises a rupturable, lubricant containing pouch located within the package and adjacent to the tip of the catheter.

13 Claims, 6 Drawing Figures

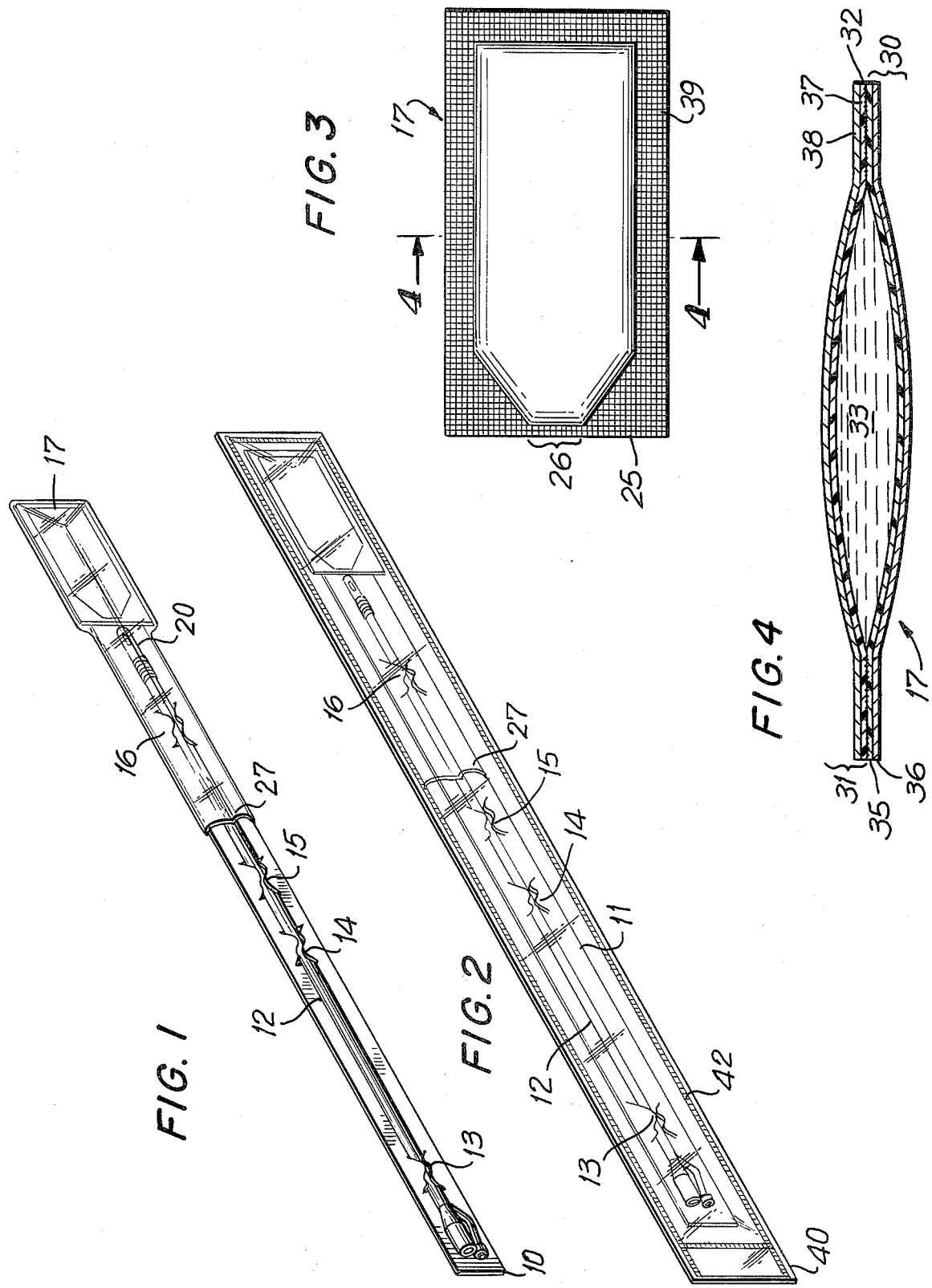

CATHETER PACKAGE

This is a continuation of application Ser. No. 337,445, filed Mar. 2, 1973 now abandoned.

BACKGROUND OF THE INVENTION

A number of medical procedures require the use of relatively flexible tubes which contain at least one longitudinal cavity or lumen. When such tubes or catheters are used by physicians, they are introduced into the body and forced along the length of a bodily passage. For example, so called venous catheters may be introduced into a vein and pushed along the length thereof until the distal end of the catheter is positioned at a desired location. Some catheters, however, are introduced into the body through essentially unwetted passages such as the urethra. Catheters of this latter type, e.g. urinary catheters, are preferably lubricated prior to introduction into the patient. In general, when a lubricated catheter is now employed, the catheter is removed from a sterile package and at least the tip thereof is lubricated by manually depositing a quantity of lubricant thereon. In practice, it has been found that such a procedure is time consuming, somewhat disorderly and increases the risk that the sterility of the catheter might be impaired.

Another problem which may be encountered when one attempts to use a catheter which should be lubricated, arises from the fact that a sterile lubricant might not be readily available. For example, a physician rendering emergency treatment may determine that the use of a catheter is required and may have a catheter available but might find that he lacks the required, or at least desired, sterile lubricant. If such a situation should arise, the physician may have to delay catheterization if substantial patient discomfort is to be avoided.

Through the use of the invention disclosed herein, many of the problems associated with the use of lubricated catheters, including those problems heretofore described, are eliminated or avoided.

SUMMARY OF THE INVENTION

In combination with a sterile catheter package, there is provided a sealed, lubricant containing pouch. One edge of the pouch is located adjacent to the tip of the catheter and the seal which is adjacent to that one edge is adapted to fail when the pouch is squeezed.

More particularly, the catheter is preferably mounted on a paperboard substrate and the combination of the substrate and the catheter are packaged within a sterile, elongated bag. Within the bag, a pouch of lubricant is maintained adjacent to but extending away from the tip of the catheter. The pouch is heat sealed and so constructed and arranged that the seal in the proximity of the edge which is adjacent to the tip of the catheter will fail when the pouch is squeezed.

Preferably, a heat shrunk film is disposed around the substrate, the catheter and the lubricant pouch.

DESCRIPTION OF THE DRAWINGS

FIG. 1 is a perspective view of one embodiment of the instant invention.

FIG. 2 is a perspective view of a package embodying the instant invention.

FIG. 3 is a plan view of a component used in the instant invention.

FIG. 4 is a sectional view taken along the section lines 4—4 of FIG. 3.

DESCRIPTION OF THE PREFERRED EMBODIMENT

Figure 5:
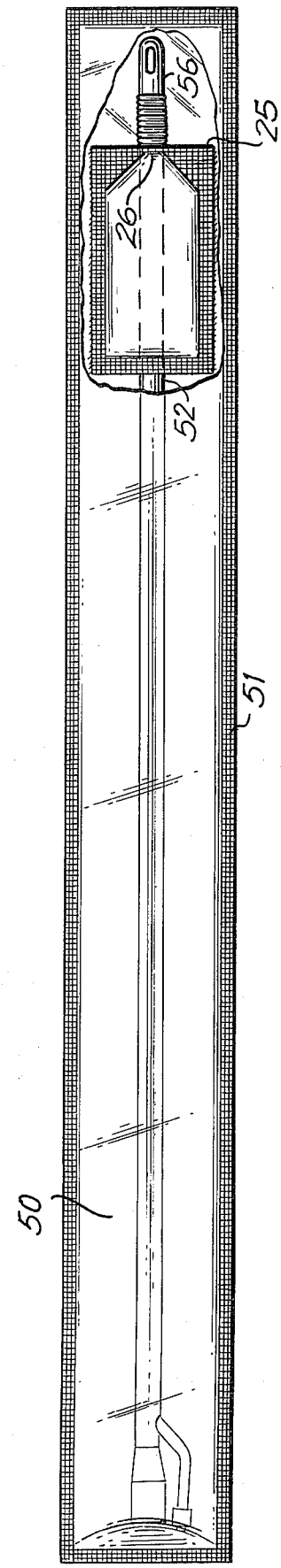
FIG. 5 is a plan view, with a portion broken away, of another embodiment of our invention.

Referring to FIG. 1, there is shown a preferred embodiment of our invention wherein a catheter 12 is positioned upon a substrate 10. The substrate 10 is preferably paperboard and may be provided with a plurality of cut-out flaps 13, 14 15 and 16. When the catheter 12 is disposed on top of the substrate 10, the catheter is placed beneath the flaps 13–16 and is thus maintained in position on the substrate 10. Of course, other appropriate means may be used to removably position or attach the catheter to the substrate. However, whatever means are used, it is preferable to provide such means adjacent to the tip 20 of the catheter 10. Thus, in FIG. 1, the flaps 16 are so located. The advantage of locating a positioning or attaching means is the proximity of the tip 20 will become apparent hereinafter.

In the preferred embodiment of FIG. 1, a pouch 17 is disposed on the substrate 10 and tandemly located with respect to the catheter 12. More particularly, it will be noted that one edge of the pouch 17, i.e. the edge 25, is positioned adjacent to the tip 20 of the catheter 12.

Surrounding one end of the substrate 10 and overlying the tip portion of the catheter 12 and a portion of the pouch 17 is a shield 27. Preferably, the shield 27 is a transparent, shrink-wrapped thermoplastic film.

Referring again to the pouch 17, there is contained therein a sterile lubricant. Additionally, the pouch 17 is so constructed and arranged that the portion of the pouch which is adjacent to the tip 20 of the catheter 12 will fail, i.e., break, when the pouch 17 is squeezed. A pouch construction which will function in this manner is shown in FIGS. 3 and 4. Referring to FIG. 4, it will be seen that, in cross-section, the pouch 17 is comprised of a lower section 30 and an upper section 31. The upper and lower sections 30, 31 are joined at 32 and thus define the cavity 33. It may also be noted that the upper section 31 and the lower section 30 are each comprised of two laminated sheets. Considering first the lower section 30, the interior sheet 35 is a thermoplastic film, for example, polyethylene. Laminated to the lower surface of the thermoplastic film 35 is an outer material 36. The material 36 is gas impermeable, for example, a metal or aluminum foil.

The upper section 31 of the pouch 17 is similarly constructed. Thus, there is provided an upper, interior thermoplastic film 37 which is laminated to an outer, gas impermeable material or film 38. As may be noted from considering FIG. 4, the upper section 31 and the lower section 30 are juxtaposed to define the cavity 33 which contains a lubricant. The pouch 17 is then closed by peripherally heat sealing the edge port on in order to bond the interior lower material 35 to the interior upper material 37 as that 32. In connection with the formation and sealing of the pouch 17, it must be remembered that the resulting pouch must be appropriately constructed so as to locally fail when pressure is applied. Thus, in the pouch embodiment shown in FIGS. 3 and 4, this objective is achieved by simultaneously satisfying two criteria. First, a relatively small area of heat seal is provided adjacent to the edge of the pouch which will be located in proximity to the tip of the catheter. Thus, it may be noted that in FIG. 3 the pouch 17 is peripherally heat sealed as indicated by the shaded port on 39. However, the area of heat seal in the region 26 is substantially less than the remainder of the peripheral heat seal.

In addition to the non-uniform heat seal area criterion described above, we have discovered that when a heat sealed pouch is employed, a rupturable heat seal may be obtained by using dissimilar thermoplastic materials on the interior of the pouch. Thus, in one embodiment of our invention, we employ a polyethylene film as the lower, interior thermoplastic material and a polypropylene film as the upper, interior thermoplastic material. Indeed, experiments conducted upon the occasion of this invention suggest that if the thermoplastic materials are not dissimilar, the peripheral bond is quite strong and it is difficult to manufacture a rupturable pouch even if the area of heat seal is appropriately sized as heretofore described.

Returning again to a consideration of the catheter package shown in FIG. 1, when the catheter 12 is to be used, a nurse or physician would squeeze the pouch 17 or roll the pouch 17, as one would roll a toothpaste tube, which action results in a failure or bursting of the heat seal adjacent to the edge 25. When the heat seal thus fails, the lubricant contained within the pouch is discharged over the tip 20 of the catheter 12 and thus the tip portion of the catheter is automatically lubricated. Additionally, if a transparent, thermoplastic, shrink-wrap film has been used as the shield 27, the discharge of the lubricant will be apparent because of the transparency of the shield. Moreover, because the shield has been shrink-wrapped around the substrate, a channel is formed adjacent to the catheter which promotes the flow of the lubricant there along.

Referring to FIG. 2, there is shown the catheter package 11 of FIG. 1 positioned within an envelope 40. The envelope 40 may be a sandwich construction comprised of a lower paper portion and an upper cellophane or thermoplastic film portion. In any event, before the catheter package is placed within the envelope 40, the catheter package and the interior of the envelope are exposed to a sterilizing gas, for example, ethylene oxide.

In this connection, it may be noted that the outer covering of the pouch 17 is preferably a gas impermeable material since sterilizing gases such as ethylene oxide may have a deleterious effect upon the lubricant. In FIG. 2 the upper portion of the envelope, for example, the transparent film portion, is shown as being peripherally heat sealed to the lower portion as at 42.

If desired, it is possible to appropriately size or dimension the envelope 40 so as to obviate the need for the shield 27. For example, one of the purposes of the shield 27 is to grip or engage, and thereby position the pouch 17. However, the pouch 17 may be positioned by bonding the pouch to the bottom of the upper surface of the envelope 40. Alternatively, the width of the pouch and the interior width of the envelope 40 may be so dimensioned that the envelope will transversely engage the pouch.

Referring to FIG. 5, there is shown another embodiment of our invention wherein the substrate is omitted. Thus, in FIG. 5, there is shown an envelope 50 which is peripherally heat sealed as at 51. A catheter 52 is contained within the envelope 50. Also contained within the envelope 50 is a lubricant containing pouch 25 of the type and construction heretofore described. Thus, the pouch 25 is adapted to fail, at the region 26 when the pouch is squeezed.

In this embodiment of our invention, as shown in FIG. 5, the pouch 25 overlies the catheter 52 rather than being tandemly disposed with respect to the catheter. However, it should be noted that the edge of the pouch 25 which is adapted to fail is located adjacent to the tip 56 of the catheter 52, i.e. the edge of the pouch is operatively positioned with respect to the catheter tip so that when the pouch 25 is squeezed, the region 26 will fail and lubricant will be deposited upon the catheter tip.

It is preferable to positively position the pouch within the envelope. Thus, the envelope may be dimensioned so as to grip or engage the pouch or the pouch may be reduced to the interior of the envelope, for example by a heat seal or through the use of a glue.

Figure 6:
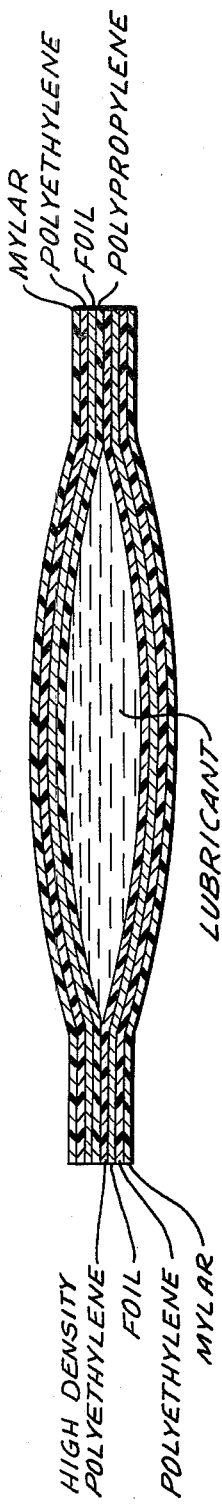
FIG. 6 is a side view, in section, of a preferred component of our invention.

Referring to FIG. 6, there is shown a side sectional view of a lubricant pouch which is so constructed and arranged as to be especially useful in combination with a catheter package of the type heretofore described. As may be noted, the catheter pouch of FIG. 6 employs upper and lower walls, each of which has a four layer construction. More particularly, it may be observed that the two inner layers of the upper and lower walls are the same as the layers employed in the pouch of FIG. 4, i.e. a polypropylene and a foil layer on the top and a polyethylene and foil layer on the bottom. Thus, the pouch of FIG. 6 will have the same rupturable capability as the pouch of FIG. 4. However, the pouch of FIG. 6 additionally includes two outer layers, viz. an outer polyethylene layer and a Mylar layer as the outer most layer. The outer polyethylene layer functions as a bonding layer to bond the Mylar film layer to the foil layer. The function of the outer most layer, i.e. the Mylar film, is to act as a thermal insulation layer. As such, if the combination of the catheter and the pouch are subjected to steam sterilization, the outer insulating film, i.e. the Mylar film, will reduce heat transfer to the foil and thereby a thermal breakdown or degradation of the lubricant may be avoided.

Although a number of embodiments of our invention have hereinbefore been described, still other variations or embodiments may be perceived by those skilled in the art without departing from the scope of our invention as defined in the claims appended hereto.

We claim:

1. In combination with a sterile catheter package which includes an envelope that surrounds a catheter contained therein, the improvement which comprises a sealed pouch of lubricant within said package, said pouch being secured at the end of said package nearest the tip of said catheter, one edge of said pouch being adjacent to the tip of said catheter and transverse to the longitudinal axis of said catheter, the pouch seal adjacent to said one edge being rupturable when said pouch is squeezed, whereby lubricant may be discharged over the tip of said catheter while said catheter is under sterile conditions.

2. The catheter package of claim 1 wherein said pouch overlies said catheter.

3. The catheter package of claim 2 wherein said pouch comprises:
   a. an interior, lower, thermoplastic material;
   b. a juxtaposed, interior, upper thermoplastic material, peripherally heat sealed to said lower thermoplastic material, the area of heat seal adjacent to the tip of said catheter being substantially less than the remainder of said peripheral heat seal, said upper and said lower thermoplastic material being dissimilar; and c. a gas impermeable material covering said upper and said lower thermoplastic material.

4. The catheter package of claim 3 wherein said pouch further comprises an outer, heat-insulating film bonded to said gas impermeable material by an interposed thermoplastic film.

5. The catheter package of claim 1 wherein said pouch is tandemly disposed with respect to said catheter.

6. The catheter package of claim 5 wherein said pouch comprises:
   a. an interior, lower, thermoplastic material;
   b. a juxtaposed, interior, upper thermoplastic material, peripherally heat sealed to said lower thermoplastic material, the area of heat seal adjacent to the tip of said catheter being substantially less than the remainder of said peripheral heat seal, said upper and said lower thermoplastic material being dissimilar; and
   c. a gas impermeable material covering said upper and said lower thermoplastic material.

7. The catheter package of claim 6 wherein said pouch further comprises an outer, heat-insulating film bonded to said gas impermeable material by an interposed thermoplastic film.

8. A catheter package which comprises:
   a. a substrate;
   b. a catheter having a tip at one end maintained in position on said substrate;
   c. a sealed pouch of lubricant positioned on said substrate, said pouch being secured on said substrate nearest said tip of said catheter, one edge of said pouch being adjacent to said tip of said catheter and transverse to the longitudinal axis of said catheter, the pouch seal adjacent to said one edge being rupturable when said pouch is squeezed, whereby lubricant may be discharged over said tip of said catheter while said catheter is under sterile conditions; and
   d. a film overlying at least the tip portion of said catheter and at least that portion of said pouch which is adjacent to said one edge.

9. The catheter package of claim 8 wherein said package is surrounded by an envelope.

10. The catheter package of claim 8 wherein said pouch overlies said catheter and comprises:
    a. an interior, lower, thermoplastic material;
    b. a juxtaposed, interior, upper thermoplastic material, peripherally heat sealed to said lower thermoplastic material, the area of heat seal adjacent to the tip of said catheter being substantially less than the remainder of said peripheral heat seal, said upper and said lower thermoplastic material being dissimilar; and
    c. a gas impermeable material covering said upper and said lower thermoplastic material.

11. The catheter package of claim 10 wherein said pouch further comprises an outer, heat-insulating film bonded to said gas impermeable material by an interposed thermoplastic film.

12. The catheter package of claim 8 wherein said pouch is tandemly disposed with respect to said catheter and said pouch comprises:
    a. an interior, lower, thermoplastic material;
    b. a juxtaposed, interior, upper thermoplastic material, peripherally heat sealed to said lower thermoplastic material, the area of heat seal adjacent to the tip of said catheter being substantially less than the remainder of said peripheral heat seal, said upper and said lower thermoplastic material being dissimilar; and
    c. a gas impermeable material covering said upper and said lower thermoplastic material.

13. The catheter package of claim 12 wherein said pouch further comprises an outer, heat-insulating film bonded to said gas impermeable material by an interposed thermoplastic film.

* * * * *